United States Patent [19]
Amer et al.

[11] Patent Number: 4,895,723
[45] Date of Patent: Jan. 23, 1990

[54] CHOLESTYRAMINE COMPOSITIONS AND METHOD FOR PREPARATION THEREOF

[75] Inventors: Moh. S. Amer, Fairfield County, Conn.; Jack C. Gray, Suffolk County, N.Y.

[73] Assignee: Amer and Company, Carpenteria, Calif.

[21] Appl. No.: 904,920

[22] Filed: Sep. 8, 1986

[51] Int. Cl.$^4$ .............................................. A61K 31/74
[52] U.S. Cl. ...................................... 424/79; 514/974
[58] Field of Search ............................................ 424/79

[56] References Cited
FOREIGN PATENT DOCUMENTS

| 896241 | 7/1983 | Belgium . | |
| 699352 | 12/1964 | Canada | 424/79 |
| 0171528 | 2/1986 | European Pat. Off. | 424/79 |
| 0227603 | 7/1987 | European Pat. Off. . | |
| 1900124 | 9/1969 | Fed. Rep. of Germany | 424/79 |
| 1181003 | 3/1967 | United Kingdom | 424/79 |

Primary Examiner—Joseph L. Schofer
Assistant Examiner—Peter F. Kulkosky
Attorney, Agent, or Firm—Samson B. Leavitt; Michael A. Leavitt

[57] ABSTRACT

Orally ingestible compositions for reduction of blood cholesterol levels comprising cholestyramine and as deodorant material a water-soluble carbonhydrate syrup such as high fructose corn syrup or a liquid alcohol polyol humectant such as glycerine. The components are blended to form a deodorized powder which may be added to water to form a beverage or mixed with an additional carbohydrate material such as polydextrose to form a unitary orally ingestible product such as a wafer.

19 Claims, No Drawings

CHOLESTYRAMINE COMPOSITIONS AND METHOD FOR PREPARATION THEREOF

This invention relates to cholestyramine compositions and to a method for preparation of such compositions.

It is well known that various diseases are caused by high cholesterol levels in the blood plasma. Indeed, the most serious and life-threatening of these may be cardiac diseases such as arterosclerosis and coronary heart disease.

Accordingly, the art has considered it highly desirable to provide compositions, particularly for oral administration, which effectively reduce the cholesterol level in the blood.

Cholestyramine, a hydrophilic polyacrylic quaternary ammonium anion exchange resin, which is described in U.S. Pat. No. 3,308,020 to Wolf et al, as well as in U.S. Pat. Nos. 3,769,399 to Hagerman et al; 3,846,541 to Howard; 4,172,120 to Todd et al; 4,252,790 to Higuchi; and 4,340,585 to Brozatta et al; is well known and accepted as very effective in reducing blood cholesterol levels. It is available commercially from the Mead-Johnson division of the Bristol-Myers Company in a powder product named "Questran".

The effectiveness of cholestyramine is based on its ability to complex with bile acids. More particularly, cholesterol is probably the sole precursor of bile acids which during normal digestion are secreted into the intestines. A major portion of the bile acids is adsorbed from the intestinal tract and returned to the liver via the enterohepatic circulation. Cholestyramine adsorbs and/or reacts, binds, combines and/or complexes with the bile acids in the intestine to form an insoluble complex which is excreted in the feces. This loss of bile acids from the system leads to an increased oxidation of cholesterol to replace the loss, with a resulting decrease in beta or low density lipoprotein plasma levels and serum cholesterol levels.

Because of its low binding capacity for bile acids, the normally recommended daily dose of cholestyramine is 8 to 16 grams. This presents a major problem since the resin has an unpleasant fishy odor, gritty texture and objectionable taste properties and patients find it extremely difficult to ingest this amount of material day after day. Attempts to increase this binding capacity of cholestyramine, and thereby enable a reduction in the daily dosage, have consistently failed.

Prior attempts to mask the objectionable properties have been counter-productive. For instance, when cholestyramine is incorporated into cookies, breads, cake products such as brownies, etc., the high saturated fat and/or sugar contents of such products tend to defeat the blood cholesterol-reducing purpose of cholestyramine and/or introduce calorie-increasing and other problems.

It is an object of this invention to provide cholestyramine compositions in which the aforesaid objectionable properties, especially the fishy odor, are effectively masked or eliminated, thereby making it palatable to users.

It is a further object of this invention to provide such improved cholestyramine compositions of relatively low calorie content and/or totally or substantially devoid of saturated fat.

It is still a further object of this invention to provide a process for preparing such cholestyramine compositions.

Another object of this invention is the provision of such improved cholestyramine compositions in diverse liquid and solid oral dosage forms.

Additional objects and advantages will be apparent from a consideration of the following description.

In accordance with certain of its aspects this invention relates to an orally ingestable composition comprising cholestyramine admixed with, per part by weight of the cholestyramine, at least one deodorizing agent selected from the group consisting of I. about 0.2 to about 4.5 parts by weight of a water-soluble carbohydrate-containing aqueous syrup, and II. about 0.2 to about 4.5 parts by weight of an alcoholic liquid polyol humectant.

Other aspects of this invention include methods for making such compositions and oral liquid and solid dosage forms thereof.

It is recognized that in U.S. Pat. No. 3,308,020 to Wolf et al, Example 7 thereof describes a therapeutic diet for treating hypercholesteremia containing Acrysol CQ, which is disclosed as an alternative to cholestyramine, and corn oil, a water insoluble liquid fat unrelated to the aqueous syrupy carbohydrate solutions employed herein.

Similar comments apply to compositions fed to the groups of rats receiving cholestyramine in Formulation C of U.S. Pat. No. 3,769,399 to Hagerman et al, which contains modified corn starch and corn oil, and to Example 9 of U.S. Pat. No. 3,383,281 to Wolf et al, referring to a therapeutic diet for treating hypercholesteremia containing corn oil and a water-insoluble stryene divinylbenzene quaternary ammonium compound.

It is also recognized that U.S. Pat. No. 4,340,585 to Borzatta et al discloses a solution of cholestyramine resin in propylene glycol for oral administration to rats. Such solution is quite different from the paste, doughy and powder compositions formed in accordance with the present invention.

The water-soluble carbohydrate in the aqueous (water) syrup which suppresses the fishy odor of cholestyramine in accordance with this invention is usually and preferably a member of the sugar family. Preferred syrups include corn (preferably high fructose) syrup, sucrose syrup, invert sugar syrup and the like. Other examples of operative water-soluble carbohydrates suitable for making such syrups include honey, molasses, glucose, maltose, dextrose, levulose, mannose and polydextrose. The carbohydrate in corn syrup may have a fructose content of about 2 to 100% by weight. It is preferred to employ corn syrup modified to contain carbohydrate having a high-fructose content of about 80-100% by weight, most preferably about 90% as in Example 1 below, in the practice of the present invention since fructose in 170% w/w sweeter than sucrose.

The carbohydrate solids content of the syrup should be sufficient to initially produce upon admixture with the cholestyramine a pasty or doughy mass, generally being at least 50 wt.%, for example about 50 to 90 wt.% solids, preferably about 65 to 85 wt.%, more preferably about 75 to 80 wt.%, and still more preferably about 77%. The amount of syrup effective for initially producing with the cholestyramine a pasty or dough mass, i.e., the syrup:cholestyramine weight ratio, is more or less dependent in any particular instance on the solids content of the syrup. Stated otherwise, the syrup solids content and the syrup:cholestyramine weight ratio are interrelated and so adjusted as to initially produce a pasty or dough mass upon admixture of the syrup with the cholestyramine. Such weight ratio may generally range from about 4.5–0.2:1, preferably about 3:1 to 1:1, more preferably about 1.8:1 to 1.2:1, still more preferably about 1.5:1.

In accordance with a preferred embodiment of this invention, the composition is prepared by blending together the appropriate ratio of cholestyramine and water-soluble carbohydrate syrup. The mixture initially formed is very sticky with a pasty or dough-like consistency. Mixing is continued to produce a light, fluffy, odorless (devoid of fishy odor) powder of homogeneous appearance. If more than light, mechanical agitation is required to produce the light, fluffy powder, the mixture may be milled, for instance in a Fitzpatrick Mill to achieve this end, and/or the above-described syrup solids content and syrup:cholestyramine weight ratios suitably adjusted.

Alternatively, and often less preferably, the cholestyramine is blended with an alcoholic liquid polyol (polyhydric alcohol) humectant to similarly form an odorless (devoid of fishy and other objectionable odors) light, fluffy powder. These humectants are well known, being generally water soluble. Normally liquid humectants such as glycerine and propylene glycol are preferred. Normally solid humectants such as sorbitol, mannitol, xylitol and the like may be employed in liquid form as aqueous solutions with solids contents in the ranges discussed above in connection with the carbohydrate syrups. Other useful humectants include low molecular weight liquid polyethylene glycol and polypropylene glycol (e.g. 400,600).

The liquid humectant:cholestyramine weight ratio may generally range from about 4.5–0.2:1, preferably about 3.0:1 to 0.4:1, more preferably about 2.0:1 to 0.5:1, and still more preferably about 0.6:1. The humectant/cholestyramine composition is prepared by mixing in the manner described above with respect to use of water-soluble carbohydrate syrup, with similar initial production of a pasty mass which upon continued mixing changes to an odorless light fluffy powder.

It will be understood that with suitable adjustment of proportions, mixtures of the carbohydrate syrup type I and liquid humectant type II deodorizing agents may be similarly blended with cholestyramine.

In the practice of the present invention it is often desirable to prepare an ultimate product which supplies about 2.7 gms. of cholestyramine. Such a non-odorous product is readily taken orally, 3–6 times daily in order to supply the normal daily prescription dosage of 8–16 gms. For example, prepackaged portions of the above described deodorant/cholestyramine powder containing 2.7 gms. of the cholestyramine can be readily dissolved in water, skimmed milk or the like to provide a readily ingested odorless beverage. In general, orally ingestible products may be prepared containing any aliquot dosage portions of the deodorant/cholestyramine powder of this invention, for example units or pieces of candy each containing sufficient powder to provide 2–3 grams of cholestyramine.

The deodorized compositions can also be readily provided with color and flavor to enhance their appeal to the user. For instance color material and/or flavor may be added, preferably to the deodorant, deodorizing agent or material, that is the water-soluble carbohydrate syrup or alcoholic polyol humectant, before blending with the cholestyramine.

Typical color material are those associated with citrus fruit, e.g. orange, yellow, green, etc. They are typically present in amounts of about 0.02 to 2.0 wt.% of the cholestyramine.

Typical flavors are those which provide mint or citrus character, e.g. peppermint, spearmint, wintergreen, clove, orange, lemon, lime, etc. They are typically present in amounts of about 0.05 to 4.0 wt.% of the cholestyramine.

The powder or beverage made therefrom may be found by some users to be somewhat "gritty" or "chalky" to the taste and feel in the mouth. This is readily and substantially overcome by including microcrystalline cellulose or a binding material (that is a gum or gum-like material) preferably with the cholestyramine prior to its mixing with the deodorizing material. Such binding materials are typically cellulose binders such as methyl cellulose, hydroxyethyl cellulose, hydroxypropyl methyl cellulose, cellulose esters, sodium carboxymethyl cellulose, etc., or polysaccharides such as the xanthamonas colloid, xanthan. The microcrystalline cellulose or binder is typically employed in amounts of about 3 to about 30% by weight of the cholestyramine, preferably about 5 to 25%. Besides reducing grittiness or chalkiness, these additives may also reduce the tendency some users have toward constipation.

Moreover, as desired, further additives may be blended into the powder of types and in amounts well accepted in the art. Such further additives may include artificial sweeteners such as sodium saccharin, sodium cyclamate, Aspartame, etc., as well as vitamins and minerals.

The deodorized composition of the present invention is also desirably formulated and/or shaped into unitary products such as granules, tablets, wafers, cookie shapes and the like.

In order to make such unitary solid consumable product from the above-described deodorant/cholestyramine odorless powder, water-soluble carbohydrate syrup as described above, in proportions sufficient to produce a "sheetable" dough, is blended into the powder in typical weight ratios of such carbohydrate syrup to deodorized powder of about 0.5–1.5:1, preferably about 0.8:1 to 1:1. Although any normally consumable water-soluble carbohydrate syrup may be used in making the unitary cholestyramine product, polydextrose syrup liquid is preferred because of its relatively low caloric nature and since relatively less of it is generally needed to produce the desired sheetable dough mass, for example polydextrose syrup:deodorized powder weight ratios of about 0.4:1 to 0.7:1, preferably about 0.5:1 to about 0.65:1.

Polydextrose, produced as described in U.S. Pat. No. 3,766,165 (1973) and 3,876,794 (1975), is a water soluble randomly bonded condensation polymer of dextrose containing minor amounts of bonded sorbitol and citric acid. Commercially available polydextrose Type N aqueous syrup (Pfizer) contains about 70% polydextrose of which 88.7% has a molecular weight (M.W.) range of about 162 to 5,000, 10% has a M.W. of about 5000 to 10,000, 1.2% has a M.W. range of about 10,000 to 16,000 and 0.1% has a M.W. range of about 16,000 to 18,000.

After blending a polydextrose syrup or the like carbohydrate syrup with the deodorized powder, a dough readily forms which can be formed, rolled, pressed or extruded into sheets. Such sheets can then be sliced or rolled more thinly and cut into any desired shapes, such as wafers which provide a dosage amount of cholestyramine.

When wafers are formed in accordance with the present invention, for instance measuring about ⅛–¼ inch in thickness and about 1.5–2.5 inches in average diameter, they possess sufficient cohesiveness and structural strength to be packaged and shipped for ultimate consumption.

Structural strength and cohesiveness of wafers may be further increased by the presence in the deodorized powder of the binding gums or gum-like materials discussed above as well as water dispersible proteins such as vital wheat gluten, sodium caseinate, egg albumin, soy isolate or the like. Typically the weight ratio of such cohesiveness-increasing additive to cholestyramine is about 0.05–0.5:1.

Moreover, structural strength and cohesiveness of wafers can also be increased by coating the wafer product in industrially recognized manners or by sandwiching the wafer as a filling between previously formed solid pieces of ingestible material.

The following Examples are only illustrative of the invention and not limitative. All amounts and proportions referred to herein and in the appended claims are by weight and temperatures are in degrees F. unless otherwise indicated.

EXAMPLE 1

Mixture A and Mixture B are prepared:

| Mixture A | |
|---|---|
| Cholestyramine | 8.0 parts |
| Methyl Cellulose (Dow A151V) | 1.0 parts |
| Xanthan Gum | 0.7 parts |
| Mixture B | |
| 90% High Fructose Corn Syrup (77% solids) | 12.0 parts |
| Liquid Orange Flavor | 0.1 parts |
| Liquid Orange Color | 0.7 parts |

Mixtures A and B are combined in a Hobart A-120 vertical mixer with a paddle, blended for 5 minutes, the sides are scraped down with the paddle and then blending is continued for an additional 10 minutes. The mixture is sticky and essentially dough-like in consistency at first but turns to a light and fluffy powder with no unpleasant odor.

Next 13.5 parts of polydextrose Type N liquid (Pfizer) are added and blended for 1 minute until a dough is formed. The sides are scraped down with the paddle and the ingredients are mixed until they are uniformly dispersed throughout the dough.

The dough is then rolled out to a uniform thickness of 3/16" using a rolling pin. In some preparations a small amount of starch is added should sticking occur. Wafers are then cut out using a "Hex" cutter measuring 1 15/16" (flat side to flat side). Each wafer weighs 11.8 grams and three wafers contain the normal daily dosage of 8.0 grams of cholestyramine.

EXAMPLE 2

Mixture A and Mixture B are prepared:

| Mixture A | |
|---|---|
| Cholestyramine | 8.0 grams |
| FMC Microcrystalline Cellulose | 0.5 grams |
| (Type B CL-611) | |
| Aspartame | 0.05 grams |
| Mixture B | |
| Glycerine (99.5%) | 4.8 grams |
| Liquid Lemon Lime | 0.1 grams |
| Liquid Mint Green | 0.05 grams |

Mixture A is blended with Mixture B in a 250 ml. glass beaker with a spatula. The mixture is paste-like at first but becomes a light and fluffy powder with no unpleasant odor as blending is continued. The deodorized light fluffy powder is added to one cup of cold tap water to produce a desirable, readily ingestible beverage containing the normal daily dosage of 8 grams of cholestyramine.

EXAMPLE 3

Mixture A and Mixture B are prepared:

| | Parts |
|---|---|
| Mixture A | |
| Cholestyramine | 8.0 |
| Xanthan Gum | 0.7 |
| Vital Wheat Gluten | 1.2 |
| Butter/Vanilla/Lemon Flavor | 0.25 |
| Mixture B | |
| Invert Sugar Aqueous Syrup (77% solids) | 12.0 |
| Liquid Yellow | 0.01 |

As in Example 1, Mixtures A and B are combined, blended with 13.5 parts of polydextrose liquid and the resultant deodorized dough rolled out and cut into wafers.

Each wafer is dipped into the following mixture:

| | Parts |
|---|---|
| Unbleached Pastry Flour | 59.9 |
| Polydextrose Powder | 30.0 |
| Safflower Oil | 8.0 |
| Potassium Bicarbonate | 1.0 |
| Anhydrous Monocalcium Phosphate | 1.1 |
| Water | 45.0 |

The dipped wafers are placed on a parchment lined baking pan and baked for 6 minutes at 400° F.

Alternatively, instead of dipping into the above mixture, each wafer is dipped in a chocolate coating mixture and heated to 115° F., drained and then cooled to set the chocolate coating.

Readily ingestible, tasty coated wafers are thus produced containing incremental dosage amounts of the cholestyramine as normally prescribed.

This invention has been disclosed with respect to certain preferred embodiments and it will be understood that various modifications and variations thereof obvious to those skilled in this art are to be included within the spirit and purview of this application and the scope of the appended claims.

We claim:

1. In a method of making orally ingestible cholestyramine-containing composition devoid of fishy odor for reducing the cholesterol level in human blood, the improvement comprising the step of blending a cholesterol-reducing agent consisting essentially of cholestyramine, which agent is capable of forming an insoluble complex with bile acids, with, approximately by weight, an amount of an aqueous syrup containing at least 65% of water-soluble sugar carbohydrate within a cholestyramine:syrup ratio ranging from 1:1 to 1:4.5 sufficient to initially form a paste or dough.

2. The method of claim 1 wherein said syrup is selected from the group consisting of corn syrup, sucrose syrup, invert sugar syrup and polydextrose syrup.

3. The method of claim 1 wherein said syrup is high fructose corn syrup.

4. The method of claim 1 wherein said syrup further contains an amount of xanthan gum or microcrystalline cellulose sufficient to minimize grittiness of solid shaped products derived from the resulting paste or dough.

5. The method of claim 1 wherein said syrup further contains an amount of a binding material selected from the group consisting of methyl cellulose, hydroxyethyl cellulose, hydroxypropyl methyl cellulose, carboxymethyl cellulose, and polysaccharides sufficient to minimize grittiness or improve structural strength of solid shaped products derived from the resulting paste or dough.

6. The method of claim 1 followed by further mixing the paste or dough to form a substantially odorless powder.

7. The method of claim 6 followed by blending the resulting powder with sufficient water soluble carbohydrate-containing syrup to form a doughy mass.

8. The method of claim 7 wherein said syrup blended with said powder contains polydextrose as the water soluble carbohydrate.

9. The method of claim 7 followed by forming said doughy mass into a solid shaped orally ingestible product.

10. The paste or dough produced by the method of claim 1.

11. The paste or dough produced by the method of claim 2.

12. The paste or dough produced by the method of claim 3.

13. The paste or dough produced by the method of claim 4.

14. The paste or dough produced by the method of claim 5.

15. The powder produced by the method of claim 6.

16. An aqueous beverage containing a dosage amount of the powder of claim 15.

17. A wafer or other solid shaped orally ingestible product derived from the paste or dough of claim 10.

18. The doughy mass produced by the method of claim 7.

19. A wafer or other solid shaped orally ingestible product derived from the doughy mass of claim 18.

* * * * *